(12) United States Patent
Takeuchi et al.

(10) Patent No.: US 9,434,977 B2
(45) Date of Patent: Sep. 6, 2016

(54) RAPID IDENTIFICATION OF ORGANISMS IN BODILY FLUIDS

(71) Applicant: AVENT, INC., Alpharetta, GA (US)

(72) Inventors: James M. Takeuchi, Woodstock, GA (US); Adrienne A. Hershey, Cumming, GA (US); Scott M. Teixeira, Cumming, GA (US); Stephanie M. Martin, Johns Creek, GA (US); Juan Pablo Aragon, Atlanta, GA (US); Cindy C. Korir-Morrison, Smyrna, GA (US); Jonathan Hofmekler, Scottdale, GA (US)

(73) Assignee: Avent, Inc., Alpharetta, GA (US)

( * ) Notice: Subject to any disclaimer, the term of this patent is extended or adjusted under 35 U.S.C. 154(b) by 273 days.

(21) Appl. No.: 13/778,619

(22) Filed: Feb. 27, 2013

(65) Prior Publication Data

US 2014/0242613 A1   Aug. 28, 2014

(51) Int. Cl.
| | | |
|---|---|---|
| *G01N 33/543* | (2006.01) | |
| *C12Q 1/06* | (2006.01) | |
| *C12Q 1/04* | (2006.01) | |
| *G01N 33/558* | (2006.01) | |
| *G01N 33/569* | (2006.01) | |

(52) U.S. Cl.
CPC . *C12Q 1/06* (2013.01); *C12Q 1/04* (2013.01); *G01N 33/54393* (2013.01); *G01N 33/558* (2013.01); *G01N 33/56911* (2013.01)

(58) Field of Classification Search
None
See application file for complete search history.

(56) References Cited

U.S. PATENT DOCUMENTS

| | | |
|---|---|---|
| 3,518,164 A | 6/1970 | Andelin et al. |
| 4,283,498 A | 8/1981 | Schlesinger |
| 4,465,485 A | 8/1984 | Kashmer et al. |
| 4,586,491 A | 5/1986 | Carpenter |
| 4,827,944 A | 5/1989 | Nugent |
| 4,932,081 A | 6/1990 | Burns |
| 4,961,432 A | 10/1990 | Guirguis |
| 5,135,490 A | 8/1992 | Strickland |

(Continued)

FOREIGN PATENT DOCUMENTS

| | | |
|---|---|---|
| EP | 0 300 221 A2 | 1/1989 |
| EP | 1 234 543 A1 | 8/2002 |

(Continued)

OTHER PUBLICATIONS

Koper, J. W. et al, "Prevention of Cross-Reactions in the Enzyme Linked Immunosorbent Assay (Elisa) for the Detection of *Staphylococcus aureus* Enterotoxin Type B in Culture Filtrates and Foods," Journal of Food Safety, vol. 2, No. 1, Jan. 1, 1980, pp. 35-45.

(Continued)

*Primary Examiner* — Rebecca Martinez
(74) *Attorney, Agent, or Firm* — Dority & Manning, P.A.

(57) ABSTRACT

There is provided a lateral flow assay that can provide an indication of Gram negative (GN) or Gram positive (GP) infection (or both) within 30 minutes, and desirably in less than 15 minutes. The immediate result would signal the presence of Gram negative bacteria, Gram positive bacteria, both Gram negative and Gram positive bacteria, or no bacteria detected. The detection level would be above a specific bacterial concentration threshold that is clinically significant infection source (e.g. 10^3 cfu/ml) versus the presence of a colonizing bacteria that is not a part of the active infection.

8 Claims, 3 Drawing Sheets

(56) References Cited

U.S. PATENT DOCUMENTS

| | | |
|---|---|---|
| 5,165,420 A | 11/1992 | Strickland |
| 5,246,012 A | 9/1993 | Strickland |
| 5,363,860 A | 11/1994 | Nakao et al. |
| 5,433,195 A | 7/1995 | Kee et al. |
| 5,595,187 A | 1/1997 | Davis |
| 5,685,843 A | 11/1997 | Enhorning |
| 5,846,183 A | 12/1998 | Chilcoat |
| 5,919,174 A | 7/1999 | Hanson |
| 6,325,785 B1 | 12/2001 | Babkes et al. |
| 6,361,505 B1 | 3/2002 | Rainen et al. |
| 6,375,625 B1 | 4/2002 | French et al. |
| 6,398,775 B1 | 6/2002 | Perkins et al. |
| 6,429,026 B1 | 8/2002 | Pettersson et al. |
| 6,632,842 B2 | 10/2003 | Chaudry et al. |
| 6,679,264 B1 | 1/2004 | Deem et al. |
| 7,018,330 B2 | 3/2006 | Alekseenko et al. |
| 7,160,248 B2 | 1/2007 | Alekseenko et al. |
| 7,270,959 B2 | 9/2007 | Hudak |
| 7,384,793 B2 | 6/2008 | McCash et al. |
| 7,517,495 B2 | 4/2009 | Wu et al. |
| 7,527,058 B2 | 5/2009 | Wright et al. |
| 8,021,873 B2 | 9/2011 | Johnson et al. |
| 2002/0123697 A1 | 9/2002 | Ishizaka et al. |
| 2003/0224000 A1* | 12/2003 | Kokai-Kun et al. ....... 424/165.1 |
| 2004/0014203 A1 | 1/2004 | Wickstead et al. |
| 2004/0228764 A1 | 11/2004 | Stephens et al. |
| 2005/0214951 A1* | 9/2005 | Nahm et al. .................. 436/514 |
| 2005/0227370 A1* | 10/2005 | Ramel ................ G01N 33/726 436/514 |
| 2005/0250141 A1* | 11/2005 | Lambert et al. .................. 435/6 |
| 2005/0272975 A1 | 12/2005 | McWeeney et al. |
| 2006/0074347 A1 | 4/2006 | Eguchi et al. |
| 2006/0292035 A1 | 12/2006 | Gould et al. |
| 2007/0213632 A1 | 9/2007 | Okazaki et al. |
| 2007/0225559 A1 | 9/2007 | Clerc et al. |
| 2008/0096236 A1* | 4/2008 | Koulchin et al. ............ 435/7.32 |
| 2008/0113391 A1 | 5/2008 | Gibbons et al. |
| 2008/0199851 A1 | 8/2008 | Egan et al. |
| 2009/0054809 A1 | 2/2009 | Morishita et al. |
| 2009/0192448 A1 | 7/2009 | Talamonti |
| 2009/0301480 A1 | 12/2009 | Elsakka et al. |
| 2009/0306544 A1 | 12/2009 | Ng et al. |
| 2009/0306545 A1 | 12/2009 | Elsakka et al. |
| 2009/0318758 A1 | 12/2009 | Farr et al. |
| 2010/0016757 A1 | 1/2010 | Greenburg et al. |
| 2010/0056387 A1 | 3/2010 | Schulz et al. |
| 2010/0174210 A1 | 7/2010 | Han et al. |
| 2010/0241091 A1 | 9/2010 | Wu |
| 2012/0196304 A1 | 8/2012 | Dees et al. |
| 2012/0282681 A1* | 11/2012 | Teixeira et al. ............ 435/287.2 |

FOREIGN PATENT DOCUMENTS

| | | |
|---|---|---|
| EP | 1 553 394 A1 | 7/2005 |
| EP | 1 867 973 A1 | 12/2007 |
| EP | 2204653 A1 * | 7/2010 |
| WO | WO 92/10971 A1 | 7/1992 |
| WO | WO 96/39917 A1 | 12/1996 |
| WO | WO 99/08731 A1 | 2/1999 |
| WO | WO 02/084266 A2 | 10/2002 |
| WO | WO 03/061453 A2 | 7/2003 |
| WO | WO 03/105941 A1 | 12/2003 |
| WO | WO 2004/055516 A1 | 7/2004 |
| WO | WO 2005/023426 A2 | 3/2005 |
| WO | WO 2005/026690 A2 | 3/2005 |
| WO | WO 2005/050165 A2 | 6/2005 |
| WO | WO 2005/094665 A2 | 10/2005 |
| WO | WO 2006/055934 A2 | 5/2006 |
| WO | WO 2007/016691 A2 | 2/2007 |
| WO | WO 2007/098184 A2 | 8/2007 |
| WO | WO 2007/109418 A2 | 9/2007 |
| WO | WO 2007/146613 A2 | 12/2007 |
| WO | WO 2008/062048 A2 | 5/2008 |
| WO | WO 2008/085228 A2 | 7/2008 |
| WO | WO 2009/002447 A1 | 12/2008 |
| WO | WO 2009/018473 A1 | 2/2009 |
| WO | WO 2009/134634 A2 | 11/2009 |
| WO | WO 2009/152104 A1 | 12/2009 |
| WO | WO 2009/152107 A1 | 12/2009 |
| WO | WO 2009/152119 A1 | 12/2009 |
| WO | WO 2010/004570 A1 | 1/2010 |
| WO | WO 2011/050110 A1 | 4/2011 |
| WO | WO 2012/150544 A1 | 11/2012 |
| WO | WO 2014/055995 A1 | 4/2014 |

OTHER PUBLICATIONS

Li, Chen-Zhong et al., "Paper Based Point-of-Care Testing Disc for Multiplex Whole Cell Bacteria Analysis," Biosensors and Bioelectronics, Elsevier, vol. 26, No. 11, Apr. 21, 2011, pp. 4342-4348.

* cited by examiner

RAPID IDENTIFICATION OF ORGANISMS IN BODILY FLUIDS

The present disclosure relates generally to the field of medicine and more particularly relates to identifying the bacterial load in a sample, e.g. in sputum.

When a patient is admitted to a hospital, or a specific unit of the hospital, e.g.; the ICU (intensive care unit), they are often tested for the presence of infection causing microorganisms in their system through blood, urine, skin, and sputum. Depending on hospital protocol this screening test is completed upon admission to the various areas of the hospital or upon clinical signs of infection including fever, increased white blood cell count, discolored sputum, purulent sputum, decreased oxygenation, hazy chest X-ray, etc.

Currently, the sputum samples are obtained via bronchoscopy, non-bronchoscopic broncheoaviolar lavage (BAL), closed suction catheter, open suction catheter, or expectorated sample. The sample is then retained in a separate sputum trap container that is connected to the sampling device through flexible tubing connections or other means. Current sputum traps are prone to leakage or spillage, causing concern to the medical personnel involved since the exact microorganisms present are unknown. The disconnection of tubing from current sputum traps is also a source for leakage.

The sample in the sputum trap is transported to the clinical microbiology laboratory for microbial testing and analysis. The sputum trap is commonly transported in a pneumatic system from the ICU to the lab. A problem that sometimes arises is that the sample can spill or leak in the pneumatic tubing as it is being transported. This can contaminate the pneumatic system, putting the integrity of other samples transported at risk and requiring a re-sampling of the patient, with its concomitant risks.

While the clinician is waiting for the microbial data to return and the patient is showing clinical signs of infection, common practice is to give the patient 3-5 broad spectrum antibiotics to cover all possible organisms that could be causing the infection. These antibiotics can have toxic side effects for the patient. For example, some antibiotics can cause harm to the function of the kidneys. Overuse of unnecessary antibiotics can cause so-called "super bugs" and antibiotic resistance, which is a well documented problem in health care. The use of these potentially unnecessary antibiotics also incurs a large cost to the hospital as these types of antibiotics are quite expensive. Furthermore, the clinician may isolate a patient that is suspected of having a resistant or highly contagious organism (e.g.; MRSA or TB), adding further expense since there is an associated cost to isolate a patient suspected of carrying a highly infectious and dangerous organism.

The first round of microbial data that a physician receives is called a Gram stain. A Gram stain identifies whether a bacterial organism is in the Gram negative (GN) or Gram positive (GP) class as well as the morphology of the bacteria (i.e. cocci, rod, etc.) This allows the clinician to remove antibiotic(s) that affect the class of organisms with which the patient is not infected. A Gram stain test takes approximately 1 hour to perform, but with transportation time of the sample and the typical lab testing back-log, our results show that most ICU clinicians receive the Gram stain results in 12-24 hours. During this time a patient is placed on the 3-5 broad spectrum antibiotics mentioned above until the clinician reviews the Gram stain results and removes 1-3 unnecessary broad spectrum antibiotics.

Many studies have tested the specificity and sensitivity of the standard Gram stain and the general consensus is that the Gram stain is about 80% sensitive and 80% specific. The Gram stain is a subjective test because the lab technician is viewing the sample under a microscope to identify the color and location of a staining dye in bacteria cells and tests results could be Gram variable, meaning the technician could not identify the bacterial Gram class. There are also several steps to complete a Gram stain that include chemical washings and dyes that are user dependent. If these steps are not followed well, the test could be less accurate. The Gram stain procedure generally includes the followings steps: 1) place a slide with a bacterial smear on a staining rack, 2) stain the slide with crystal violet for 1-2 minutes, 3) pour off the stain, 4) flood slide with Gram's iodine for 1-2 min., 5) pour off the iodine, 6) decolorize by washing the slide briefly with acetone (2-3 seconds), 7) wash slide thoroughly with water to remove the acetone—do not delay with this step, 8) flood slide with safranin counter stain for 2 min., 9) wash with water, 10) blot excess water and dry by hand over (Bunsen) flame.

The second round of microbial data that a physician receives is called a microbial specificity. These results are obtained in 24-48 hours and require culturing of the organisms on an agar plate. Microbial specificity identifies the exact organism(s) that are causing the infection and the concentration of that organism(s) in a quantitative or semi-quantitative fashion. These results allow the clinician to change the broad spectrum antibiotics to antibiotics targeted for the specific organism that is causing the infection. The clinician may also wait to change antibiotics if the patient is improving or until further results are obtained.

The third round of microbial data that a physician received is call antibiotic sensitivities. These results are obtained in 48-72 hours and require testing the cultured sample against known antibiotics to determine the resistance pattern of the organism. Once it is know what antibiotics the organism is sensitive to or will kill the organism(s), the clinician can change to one targeted antibiotic to treat the infection.

Thus, there remains a need in the art for a microbial identification system that is easy enough to be performed at the bedside and that provides results quickly enough to give the physician the information needed to decrease the amount of antibiotics that are prescribed to the patient or give a more specific antibiotic to treat the infection. The suitable device will improve the time it takes for the physician to receive microbial results and allow the physician to make better antibiotic prescription choices to decrease antibiotic resistance, decrease toxicity for the patient, potentially improving patient outcome, saving time in beginning proper treatment and saving money currently used on inappropriate medication.

SUMMARY

In response to the difficulties and problems discussed herein, the present disclosure is for a lateral flow assay device that can conduct a test to provide an indication of Gram negative (GN) or Gram positive (GP) infection (or both) within 30 minutes, and desirably in less than 15 minutes. The immediate test would signal the presence of Gram negative bacteria, Gram positive bacteria, both Gram negative and Gram positive bacteria, or no bacteria detected. The detection level would be above a specific bacterial concentration threshold that is clinically significant infection source (e.g. 10^3 cfu/ml) versus the presence of a colonizing bacteria that is not a part of the active infection.

This device could also be used as a screening tool to be used upon admittance to the hospital or admission to a specific unit of the hospital to determine if the patient is colonized with a clinically significant concentration of bacteria. This information would allow the clinician to isolate or treat a patient before clinical signs of infection are obvious. This early information could also help a hospital determine if a patient obtained a hospital acquired infection (HAI) or already had an infection prior to admission, called a community acquired infection (CAI) for public reporting and billing purposes.

The test and all the needed reagents to complete the test can be integrated into the device so no additional or separate processing is needed. The device includes reagents, a lateral flow assay strip, antibodies and conjugates. Once properly mixed with reagents (if necessary), the sample is directed to the proximal end of a lateral flow assay (LFA) strip within the device. The sample then is exposed to the test strip for an hour or less, desirably about 30 minutes or even less, and most desirably less than 15 minutes. At the end of that time period, a detector may read the presence of a colorimetric, magnetic or florescent test line at a specific intensity range and output that result onto a digital display. The intensity of the capture antibody test line is important to prevent the system from reading slight cross reactivity of the test. While some test lines may be read by the unaided human eye, a digital display is desired so the subjectivity of the user (i.e. nurse or respiratory therapist) in reading the intensity of test lines is reduced. Additionally, the device should have a 1 to 2 year shelf life for successful commercial application.

BRIEF DESCRIPTION OF THE DRAWINGS

A full and enabling disclosure of the subject matter, including the best mode thereof, directed to one of ordinary skill in the art, is set forth more particularly in the remainder of the specification, which makes reference to the appended figures in which.

DETAILED TECHNICAL DESCRIPTION

Reference now will be made in detail to various embodiments of the disclosed subject matter, one or more examples of which are set forth below. Each example is provided by way of explanation, not limitation. In fact, it will be apparent to those skilled in the art that various modifications and variations may be made in the present disclosure without departing from the scope or spirit of the subject matter. For instance, features illustrated or described as part of one embodiment, may be used on another embodiment to yield a still further embodiment. Thus, it is intended that the present disclosure covers such modifications and variations as come within the scope of the appended claims and their equivalents.

This disclosure describes a device to rapidly classify bacteria in a sample of a bodily fluid as either Gram positive (GP) or Gram negative (GN). Such fluids include respiratory fluids (e.g. from the lung, throat, nasal cavity), digestive fluids, blood, spinal fluids, etc. A sample from the lungs, for example, can originate from the upper airway (e.g. expectorated sputum), but is desirably from the lung. A bronchoalveolar lavage (BAL), both bronchoscopic and non-bronchoscopic/blind, is a common procedure used to acquire lung sputum samples from ventilated patients. One embodiment of this device interfaces directly with a sputum collection container, although it should be understood that it can be used as a stand-alone unit, either at the bedside or in the laboratory/field.

Figure 1:
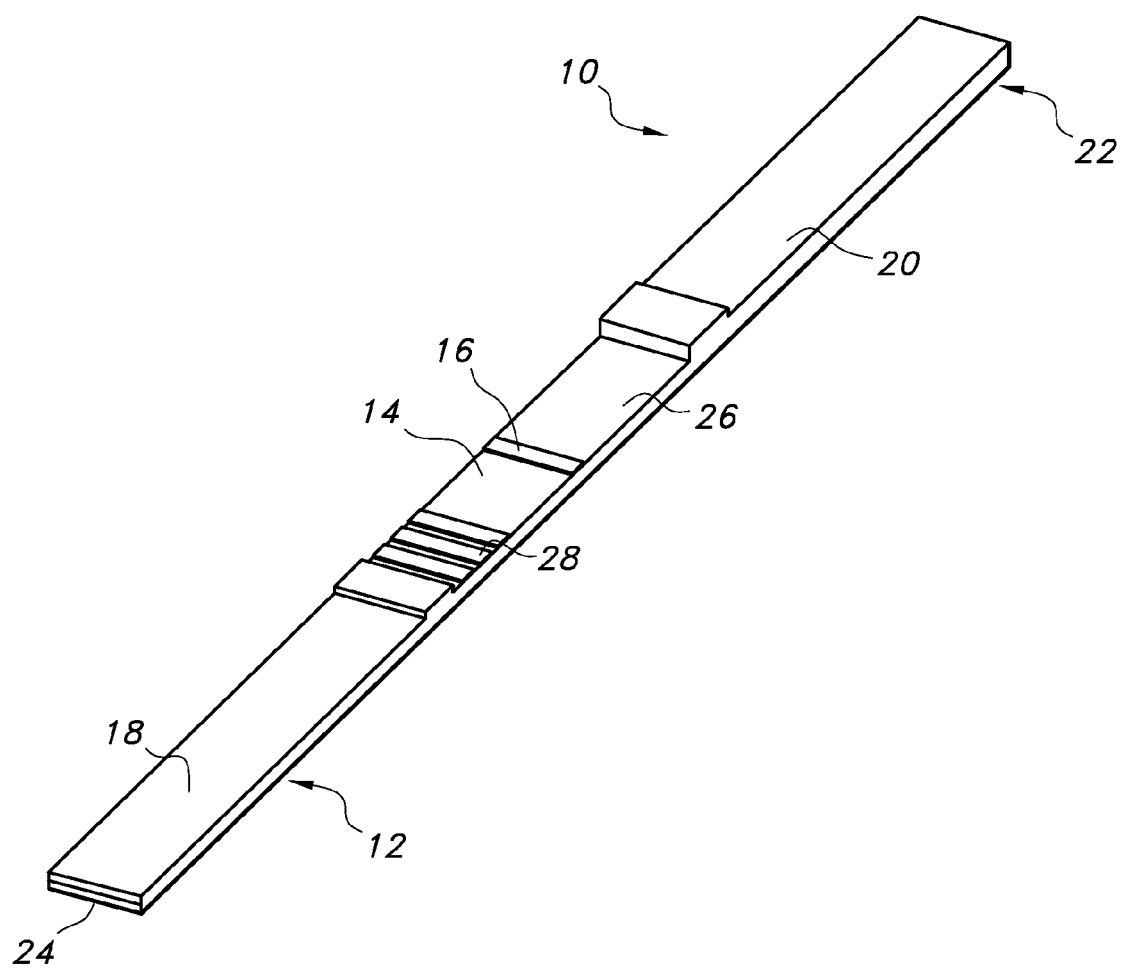
FIG. 1 is a perspective view of one embodiment of a test strip that may be used in a lateral flow assay device.
Figure 2:
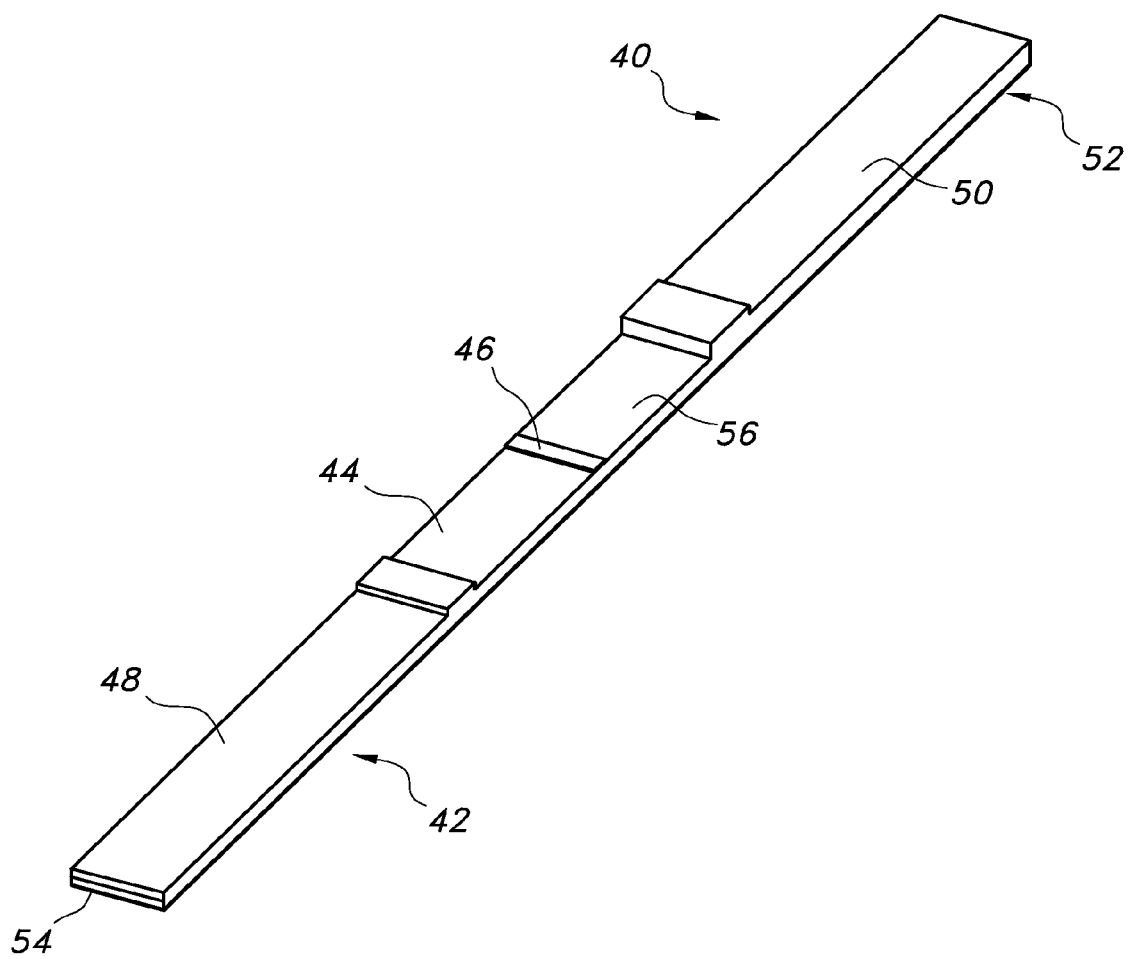
FIG. 2 is a perspective view of another embodiment of a test strip that may be used in a lateral flow assay device.

The device utilizes membrane-based lateral flow immunoassay (also known as the "assay") technology to perform the Gram classification test. One or more multi-component test strips are used to receive the sample and perform the assay. In one embodiment of this device, two individual, discreet test strips are employed: one specifically designed for GN detection (FIG. 1) and one specifically designed for GP detection (FIG. 2). Both test strips incorporate protein detection via an antibody-antigen sandwich arrangement. It should be understood that other arrangements are possible (e.g. non-sandwich) and furthermore, that the individual GP and GN test strips are not required to utilize the same arrangement simultaneously.

Each test strip has both capture and detection antibodies, both of which may be the same. For both cases, matched antibody pairs are used. The antibodies can be either monoclonal or polyclonal and can be derived from any common host sources. One embodiment of the device includes two monoclonal antibodies targeting lipoteichoic acid (LTA) and peptidoglycan of S. aureus for GP detection and a combination of one monoclonal antibody targeting lipopolysaccharide (LPS) and one polyclonal antibody targeting multiple Klebsiella antigens for GN detection. Furthermore, the detection antibodies are desirably conjugated (attached) to colloidal gold nanoparticles and placed on the test strip to result in an assay with at least one visual signal. The nanoparticles and attached antibodies are known as "the conjugate". Gold particles of approximately 40 nanometers (nm) in size are desirably used but other sizes between about 20 and 80 nm are feasible as well. Other possibilities with which to conjugate the detection antibodies include latex particles between about 100 and 300 nm, magnetic particles and fluorescent particles.

Each test strip 10, 40 is assembled and laminated from a series of discreet components. A backing card 12, 42 serves as the physical support for the other components, and this is commonly made from Mylar, though other materials may also be used. A porous matrix, 14, 44 e.g. nitrocellulose membrane, cellulose, porous polyethylene pads, and glass fiber filter paper is either laminated or directly cast onto a region of the backing card 12, 42. (The terms "nitrocellulose membrane" or "nitrocellulose" are used to represent suitable porous matrices.) The nitrocellulose contains the capture antibodies.

The capture antibodies are immobilized in a specific detection zone, desirably as a test line 16, 46 on the porous matrix 14, 44 via standard liquid dispensing equipment, including both contact and non-contact heads, as well as spraying. In one embodiment the capture antibodies form a stripe on and/or in the matrix to yield a test line 16, 46 of approximately 1 mm in width perpendicular to the longest dimension of the matrix. It has been demonstrated that larger pore size matrices improve sample flow through the system and allow for samples with whole cell organisms to be tested without the need for any sample processing steps. An exemplary nitrocellulose for this application has a measured flow rate between 40-75 cm/4 sec in the longest dimension of the matrix. Specific commercial examples include Prima 40 (GE Whatman) and 70CNPH-N-SS40 (MDI).

In one embodiment, a conjugate pad 18, 48 is used to receive the sample. As can be seen in FIGS. 1 and 2, the conjugate pads 18, 48 are supported on their respective backing cards 12, 42 proximal to the porous matrix 14, 44. The conjugate pad 18, 48, which may be glass fiber (e.g. G041 Glass Fiber Conjugate Pads, from Millipore), is used to initially contain the conjugate (e.g. detection antibodies and gold nanoparticles). The conjugate is immobilized on the conjugate pad 18, 48 until coming into contact with the sample. The conjugate can be placed onto the conjugate pad using a liquid carrier by several methods including spraying, striping, and soaking. In addition to the conjugate, the conjugate pad 18, 48 can have dried chemicals (e.g. surfactants) that aid in sample flow, particularly for those samples with high viscosity, elasticity, or organism counts. The addition of chemicals can be accomplished with the same methods. Lastly, there is a physical overlap and contact between the conjugate pad 18, 48 and the matrix 14, 44 that allows for fluid communication between them and allows the assay to run correctly.

Alternative embodiments may have an additional and separate sample pad positioned at the proximal end of the strip to receive the sample and be in physical contact with the conjugate pad to allow for fluid flow through the test strip. The sample pad may be made of conventionally known materials, e.g. commonly available cellulose materials.

A wicking pad 20, 50 for each strip 10, 40 is located at the distal end 22, 52 of the backing card 12, 42 and is used to draw the fluid sample through the system by capillary action. The sample is deposited near or on the proximal end 24, 54 of the test strip 10, 40. The wicking pad 20, 50 is an absorptive material and can be made via a number of different cellulosic materials and can vary in size and absorptive capacity as generally conventionally known. There is an overlap between the wicking pad 20, 50 and the porous matrix 14, 44 that allows for fluid communication. A suitable example material is A22 Absorptive Paper (Ahlstrom).

In some embodiments, a "running buffer" reagent in liquid form is used to help facilitate sample flow through the test strip 10, 40 and promote even, uniform color change in the test line. This buffer is water-based and has proteins (e.g. Bovine serum albumin, BSA) and surfactants (e.g. Tween 20). It is desirably mixed with the sample prior to addition to the test strip 10, 40 either via mechanisms that are part of the sampling device or through stand-alone actions such as pipetting. Alternatively, it is possible to add the running buffer to the test strip 10, 40 immediately after the sample has been introduced to the test strip 10, 40 either via mechanisms that are part of the device or through stand-alone actions such as pipetting.

In one format, a 2:1 ratio is used; 2 parts sample to 1 part running buffer, although other combinations are possible, including a range between 4:1 and 1:2 (sample: running buffer). In some embodiments 100 µl of sample is mixed with 50 µl of running buffer for each assay. The total volume of fluid applied to a single test strip can vary depending on the material selection of individual test strip components.

One feature unique to the GN (FIG. 1) assay is the need to prevent GP organisms cross-reacting to the GN antibodies on the GN test strip 10. There are several potential causes for this cross-reaction, including Protein A from *Staphylococcus* species and Protein G from *Streptococcus* species. Several arrangements have been found to be effective at reducing the GN test line signal from these agents; in some embodiments, targeting antibodies are immobilized on the test strip 10 in a zone prior to the test line 16 with respect to the proximal end 24 of the strip 10, and are termed "guard lines" 28 as illustrated in FIG. 1. Suitable antibodies for these guard line can bind either Protein A and Protein G specifically to capture them, or can effectively neutralize the reactivity of whole cell *Staphylococcus* and whole cell *Streptococcus*. Additionally, other anti-GP antibodies (e.g. Rabbit polyclonal antibodies developed against whole cell *Enterococcus faecium*)) have been shown to be effective. There is no preference of antibody type (e.g. monoclonal vs. polyclonal, host animal, etc.) for this application. By using this configuration, the cross-reactive factors present in the sample are "trapped" before the test line 16 and thus do not contribute to the test line signal. One or more of these guard lines 28 can be incorporated into the test strip 10 on the nitrocellulose via striping, spraying, or other similar conventionally known methods.

Another way of preventing GP organisms from cross-reacting to the GN antibodies is to use targeting antibodies in liquid form instead of immobilizing them in a defined zone on the test strip. In this embodiment, these targeting antibodies are introduced to the sample prior to addition to the test strip and the sample must be segregated between test strips 10, 40 so as to not interfere with the GP assay. Addition to the sample of targeting antibodies in a liquid carrier does not require additional mixing or incubation time, although the inclusion of both is possible.

Another way to reduce GP organism cross-reactivity on GN test strips is to modify the physical structure of the capture antibodies in the test line. Protein A and Protein G are known to bind to the FC portion of the antibodies on the test line. Removing this portion and only including the remaining F(ab')2 region in the antibodies of the test line 16 has been demonstrated to be effective at removing the cross-reactive signal while maintaining the true detection of GN organisms. This modified antibody (FC portion removed), once prepared, can be applied to and immobilized on the test strip 10 in the same manner as unmodified antibodies. Lastly, as it relates to this cross-reactivity, it should be noted that any combination of these embodiments can be employed together and simultaneously.

Confirmation that the appropriate amount of sample and conjugate have passed through the system is also desirable. This confirmation can involve a physical zone on the test strip 10, 40 distal to the test line 16, 46 that forms a visible signal with a specified amount of sample and/or conjugate exposure. This zone can contain either a specific antigen (e.g. Protein A) that is known to bind the conjugate antibodies or a separate antigen that requires a non-specific conjugate antibody to be added to the test strip 10, 40. In both cases, the formation of a visible signal, e.g. a line of particular intensity, signifies a proper assay. This line is referred to as the control line 26, 56 and is desirably located after the test line 16, 46. Alternatively, the confirmation can be accomplished through an associated reader (not shown) which is able to assess sample and conjugate flow via either reflectance or transmission measurements.

Figure 3:
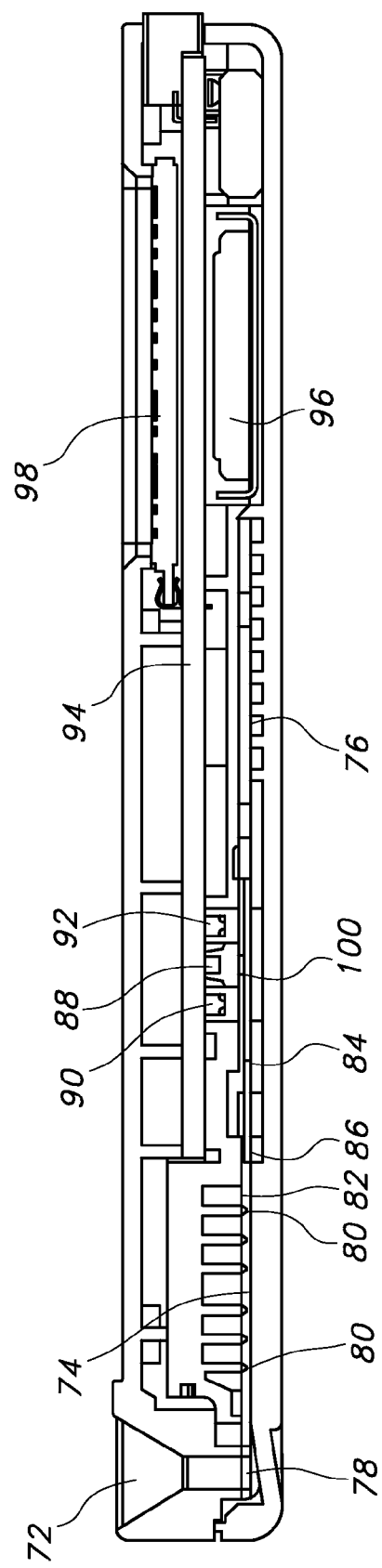
FIG. 3 is a cross-sectional view of a lateral flow assay device.

In order to prevent additional fluid from flooding the strip 76 (a known problem with lateral flow assays) and ameliorate flow onto the strip, the device can include strip compression features as shown in FIG. 3. The first compression feature is a well 72 above the conjugate pad 74 that prevents a large release of sample from initially flooding this pad 74 and having the sample transfer off the strip 76 and onto uncontrolled surfaces. This can be further enhanced by containing the end of the proximal end 78 of the strip 76 in a pocket. A second compression feature is a set of one or more ribs 80 against the upper surface 82 of the strip 76 over the conjugate pad 74. The ribs 80 allow some of the sample that is added to the conjugate pad 74 to accumulate on the surfaces of the pad 74 and the upstream rib(s) 80 while staying on the strip 76 and thus allow the gold conjugate to solubilize and mix effectively before wicking onto and through the nitrocellulose membrane 84. The final compression feature is at the conjugate pad 74 and nitrocellulose membrane 84 interface 86. This feature acts as a final regulator to encourage the sample to flow through the nitrocellulose 84 and not remain on the surface 82 and flood the system.

The result of the assay is able to be read and interpreted visually or with the inclusion of a reader. The inclusion of a reader system can take the form of either an integrated unit or a stand-alone unit. For a visual assay system based on colloidal gold, either reflectance or transmission-based measurements are possible. Additionally, reader measurements can be collected kinetically as the assay is running or at the end of a specified time once the assay has completed.

While the human eye or any number of commercially available lateral flow assay scanners may be capable of reading the test line after formation, a desirable embodiment would include a disposable integrated electronic reader. This electronic reader could include more than one or differing types of lateral assay sensors.

The simplest arrangement for an electronic reader would be an optical sensor arrangement. A light emitting diode (LED) 88, for example, would emit light onto the test line 100 and a photo-detector 90 could capture the optical density of the test line 100 being reflected. To eliminate background noise and imperfections of the strip 76 and sample, another photo-detector 92 could determine the optical density of the background noise of the strip and subtract this reading level from the test line reading level to produce a reading of the sample alone. All the components used for a digital reader could be mounted and or attached to a printed circuit board 94 including the LED(s), photo-detector(s), micro-controller chip, energy source (e.g. battery) 96, outputs (e.g. LED or LCD display) 98, and other components (e.g. resistors and capacitors).

Desired features to GP/GN Classification:

Detection/capture antibodies targeting common, bacterial surface antigens like LTA (GP) and LPS (GN).

Flow control to enable samples with a wide range of characteristics to be run:

Large pore size nitrocellulose.

Addition of chemicals/surfactants, both in the running buffer and the test strip pads, to facilitate flow.

Housing configuration—inclusion of compression points, both on the conjugate pad and the overlap between materials.

Mechanisms to reduce the cross reactivity of GP organisms to GN antibodies.

Table 1 below provides exemplary materials that may be used for the production of a test strip for the detection of Gram positive bacteria. Table 2 below provides exemplary materials that may be used for the production of a test strip for the detection of Gram negative bacteria.

TABLE 1

GP Assay Specifications

| | |
|---|---|
| Nitrocellulose | MDI 70CNPH-N-SS40, 2.5 cm |
| Test Line 1 | Anti-GP antibody, e.g. Mouse monoclonal antibodies raised against whole cell *S. aureus* cells |
| | Mouse monoclonal antibodies raised against whole cell *S. epidermidis* cells |
| | 1-3 mg/ml in 1X PBS |
| Control Line | None |
| Top Pad | Ahlstrom 222, 27 mm |
| Conjugate Pad | G041 glass fiber (27 mm) treated with 150 mM NaCl & 0.5% Triton X-100 |
| | Sprayed with 40-80 gold units (GU) of gold conjugate |
| Gold Conjugate | 40 nm gold colloid conjugated to anti-GP antibody, e.g. Mouse monoclonal antibodies raised against whole cell *S. aureus* cells |
| | Mouse monoclonal antibodies raised against whole cell *S. epidermidis* cells |
| | 10% sucrose |
| Sample Pad | None |
| Running Buffer | 50 µl added to 100 µl sample |
| | Composition: |
| | 50 mM Tris, possible range 25 mM-200 mM |
| | 150 mM NaCl, possible range 50 mM-1.0M |
| | 1% BSA, possible range 0.1%-2% |
| | 1% Tween 20, possible range 0.1%-2% |
| | pH 8.0, possible range 7.0-10.0 |

TABLE 2

GN Assay Specifications

| | |
|---|---|
| Nitrocellulose | MDI 70CNPH-N-SS40, 2.5 cm |
| Test Line 1 | Anti-GN antibody, e.g. Mouse monoclonal antibodies raised against whole cell *E. coli* cells |
| | Rabbit polyclonal antibodies raised against whole cell *K. pneumoniae* cells. |
| | 1-3 mg/ml in 1X PBS (phosphate buffered saline) |
| Guard Lines | Anti-GP antibody, e.g. Rabbit polyclonal antibodies developed against whole cell *Enterococcus faecium* |
| | Mouse monoclonal antibodies raised against whole cell *S. aureus* cells 4.5 mg/ml (3 guard lines total) |
| Control Line | None |
| Top Pad | Ahlstrom 222, 27 mm |
| Conjugate Pad | G041 glass fiber (27 mm) treated with 150 mM NaCl & 0.5% Triton X-100 |
| | Sprayed with 40-80 gold units (GU) of gold conjugate |
| Gold Conjugate | 40 nm gold colloid conjugated to anti-GN antibody, e.g. Mouse monoclonal antibodies raised against whole cell *E. coli* cells |
| | Rabbit polyclonal antibodies raised against whole cell *K. pneumoniae* cells. 10% sucrose |
| Sample Pad | None |
| Running Buffer | 50 µl added to 100 µl sample |
| | Composition: |
| | 50 mM Tris, possible range 25 mM-200 mM |
| | 150 mM NaCl, possible range 50 mM-1.0M |
| | 1% BSA, possible range 0.1%-2% |
| | 1% Tween 20, possible range 0.1%-2% |
| | pH 8.0, possible range 7.0-10.0 |

While the subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. A lateral flow assay for detecting the presence or quantity of bacteria within a sample, the lateral flow assay comprising:
   an assay device; and
   a test strip inserted into said assay device, said test strip having capture antibodies and detection antibodies, said detection antibodies immobilized in a specific zone on a proximal end of said test strip, said capture antibodies immobilized in a detection zone separate from and distal to the detection antibodies;
   said test strip further comprising a conjugate pad disposed to receive a test sample, said detection antibodies immobilized on said conjugate pad;
   said assay device further comprising a well disposed above said conjugate pad so as to prevent a large release of the sample from initially flooding the conjugate pad and a plurality of spaced-apart ribs disposed above and axially along said conjugate pad downstream of the well; said ribs pressed onto an upper surface of said conjugate pad.

2. The lateral flow assay of claim 1, wherein said detection zone comprises a test line in a distal area thereof.

3. The lateral flow assay of claim 1, wherein said detection antibodies are conjugated to colloidal gold or latex nanoparticles.

4. The lateral flow assay of claim 3, wherein said colloidal gold nanoparticles are between 20 and 80 nm in size.

5. The lateral flow assay of claim 1, wherein said detection antibodies include two monoclonal antibodies targeting lipoteichoic acid (LTA) and peptidoglycan of *S. aureus* for GP detection.

6. The lateral flow assay of claim 1, wherein said detection antibodies include one monoclonal antibody targeting lipopolysaccharide (LPS) and one polyclonal antibody targeting multiple *Klebsiella* antigens for GN detection.

7. The lateral flow assay of claim 6, further comprising targeting antibodies on said test strip in a zone between said detection antibodies and said capture antibodies adapted to bind Protein A or Protein G or to neutralize the reactivity of whole cell *Staphylococcus* and whole cell *Streptococcus*.

8. The lateral flow assay of claim 1, wherein the test strip detects bacteria within a sample of respiratory fluid.

* * * * *